United States Patent [19]

Thorsett et al.

[11] 4,316,896
[45] Feb. 23, 1982

[54] AMINOACID DERIVATIVES AS ANTIHYPERTENSIVES

[75] Inventors: Eugene D. Thorsett, Fanwood; Arthur A. Patchett; Elbert E. Harris, both of Westfield; Alan L. Maycock, Fanwood, all of N.J.

[73] Assignee: Merck & Co., Inc., Rahway, N.J.

[21] Appl. No.: 940,412

[22] Filed: Sep. 7, 1978

[51] Int. Cl.$^3$ .............................................. C07D 277/20
[52] U.S. Cl. .................................. 424/200; 424/211; 548/201; 548/341; 260/943; 260/326.13 R; 260/326.2
[58] Field of Search ............... 260/306.7 C, 326.13 R, 260/326.2, 943; 548/201, 341; 424/246, 274, 200, 211

[56] References Cited

U.S. PATENT DOCUMENTS

| 3,306,898 | 2/1967 | Sehring et al. | 260/943 |
|---|---|---|---|
| 3,674,871 | 7/1972 | Evans | 424/270 |
| 3,800,010 | 3/1974 | Nachbur et al. | 260/943 |
| 4,207,323 | 6/1980 | Beattie et al. | 424/270 |

OTHER PUBLICATIONS

Lowy et al., An Introduction to Organic Chemistry, p. 213 (1945).
Ondetti, Paper presented at Gordon Research Conference on Medicinal Chemistry at Colby-Lawyer College (N. H.) Jul. 31, 1978.

*Primary Examiner*—Nicholas S. Rizzo
*Attorney, Agent, or Firm*—Salvatore C. Mitri; Michael C. Sudol, Jr.

[57] ABSTRACT

The invention relates to new phosphoryl aminoacid derivatives and related compounds which are useful as antihypertensives.

9 Claims, No Drawings

AMINOACID DERIVATIVES AS ANTIHYPERTENSIVES

BACKGROUND OF INVENTION

The invention in its broad aspects relates to phosphonic-aminoacid compounds and derivatives thereof which are useful as converting enzyme inhibitors and as antihypertensives. The compounds of this invention can be shown by the following formula:

$$R_1-O-\underset{\underset{R_2}{\overset{|}{O}}}{\overset{\overset{O}{\|}}{P}}-X-(CH_2)_n-\overset{\overset{R}{|}}{CH}-\overset{\overset{O}{\|}}{C}-N\overset{R_3}{\underset{\underset{CO_2H}{|}}{\diagdown}}\overset{}{\diagup}\overset{}{CH-R_4} \quad (I)$$

wherein n is 0 or 1

R is hydrogen, lower alkyl, phenyl lower alkyl, hydroxy phenyl lower alkyl, hydroxy lower alkyl, amino-lower alkyl, guanidino lower alkyl, imidazoyl lower alkyl, indolyl lower alkyl, mercapto lower alkyl, lower alkyl mercapto lower alkyl;

$R_3$ is hydrogen;

$R_4$ is hydrogen, lower alkyl, phenyl lower alkyl, hydroxy phenyl lower alkyl, hydroxy lower alkyl, amino-lower alkyl, guanidino lower alkyl, guanidino lower alkyl, imidazoyl lower alkyl, indolyl lower alkyl, mercapto lower alkyl, lower alkyl mercapto lower alkyl;

$R_3$ and $R_4$ may be connected together to form an alkylene bridge of from 2 to 4 carbon atoms or an alkylene bridge of from 2 to 3 carbon atoms and one sulfur atom;

X is O, $NR^5$, S where $R^5$=H or lower alkyl;

$R_1$ is hydrogen, lower alkyl, aralkyl or aryl;

$R_2$ is hydrogen, lower alkyl, aralkyl or aryl and pharmaceutically acceptable salts thereof.

The lower alkyl groups represented by any of the variables include straight and branched chain hydrocarbon radicals from one to six carbon atoms, for example, methyl, ethyl, propyl, isopropyl, butyl, isobutyl, t-butyl, pentyl, isopentyl, hexyl, heptyl and the like. The aralkyl groups represented by any of the above variables have from one to four carbon atoms in the alkyl portion thereof and include for example, benzyl, p-methoxy benzyl and the like.

Aryl wherever it appears is represented by phenyl or substituted phenyl wherein the substituent is halo, lower alkoxy or lower alkyl.

The R and $R_4$ substituted lower alkyl moieties are exemplified by groups such as

[structures: imidazolylmethyl, indolylmethyl, furylmethyl]

$HO-CH_2-$, $HS-CH_2-$, $H_2N-(CH_2)_4-$, $CH_3-S-(CH_2)_2-$, $H_2N-(CH_2)_3-$, $$H_2N-\overset{\overset{NH}{\|}}{C}-NH-(CH_2)_3-$$

and the like.

$R_3$ and $R_4$ when joined through the carbon and nitrogen atoms to which they are attached may form a 4 to 6 membered ring which may contain one sulfur atom; a preferred ring has the formula:

$$-N\overset{\diagup\!\!\!\!\cdot-Y}{\underset{\underset{COOH}{|}}{\diagdown\!\!\!\!\cdot}}$$

where Y is $CH_2$ or S.

Preferred are those compounds of Formula I wherein
X=O, $NR_5$
Y=$CH_2$ or S;
R=lower alkyl or phenyl ($C_{1-4}$) alkyl;
$R_1$ and $R_2$ are as previously defined;
$R_3$ and $R_4$ are joined to form an alkylene bridge of from two to four carbon atoms or an alkylene bridge of from two to three carbon atoms and one sulfur atom but preferably where $R_3$ and $R_4$ are joined to form the preferred ring formula shown above.

Still more preferred compounds are those preferred compounds of Formula I wherein further R is methyl;
X=O or NH and
n=0.

The products of Formula (I) and the preferred subgroups can be produced by one or more of the methods depicted in the following equations:

Method 1

$$\underset{(II)}{\overset{\overset{R_5}{|}}{H}N-(CH_2)_n-\overset{\overset{R}{|}}{CH}-\overset{\overset{O}{\|}}{C}-\overset{\overset{R_3}{|}}{N}-\overset{\overset{R_4}{|}}{CH}-COOH} \xrightarrow[MgO]{POCl_3}$$

$$\underset{(III)}{-O-\overset{\overset{O}{\|}}{\underset{\underset{O^-}{|}}{P}}-\overset{\overset{R_5}{|}}{N}-(CH_2)_n-\overset{\overset{R}{|}}{CH}-\overset{\overset{O}{\|}}{C}-\overset{\overset{R_3}{|}}{N}-\overset{\overset{R_4}{|}}{CH}-COO^-}$$

Compound (II) is condensed with phosphorous oxychloride by the general method of T. Winnick and E. M. Scott, Arch. Biochem. 12, 201 (1947).

Method II $$\underset{(IV)}{R_1-O-\overset{\overset{O}{\|}}{\underset{\underset{R_2}{|}}{P}}-Cl} +$$

$$\underset{(V) \cdot HCl}{\overset{\overset{R_5}{|}}{H}N-(CH_2)_n-\overset{\overset{R}{|}}{CH}-\overset{\overset{O}{\|}}{C}-\overset{\overset{R_3}{|}}{N}-\overset{\overset{R_4}{|}}{CH}-COOR_6} \xrightarrow[CH_2Cl_2]{Et_3N}$$

$$\underset{(VI)}{R_1-O-\overset{\overset{O}{\|}}{\underset{\underset{OR_2}{|}}{P}}-\overset{\overset{R_5}{|}}{N}-(CH_2)_n-\overset{\overset{R}{|}}{CH}-\overset{\overset{O}{\|}}{C}-\overset{\overset{R_3}{|}}{N}-\overset{\overset{R_4}{|}}{CH}-COOR_6} \xrightarrow{OH^-}$$

$$\underset{(VII)}{R_1O-\overset{\overset{O}{\|}}{\underset{\underset{OR_2}{|}}{P}}-\overset{\overset{R_5}{|}}{N}-(CH_2)_n-\overset{\overset{R}{|}}{CH}-\overset{\overset{O}{\|}}{C}-\overset{\overset{R_3}{|}}{N}-\overset{\overset{R_4}{\|}}{CH}-COO^-} \longrightarrow$$

-continued

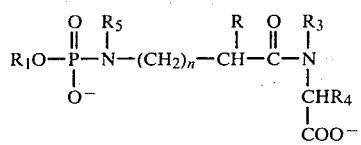

$R_6$ = alkyl or aralkyl.

Compound (V), an ester hydrochloride of compound (II), is condensed in an inert solvent such as methylene chloride with the phophochloridate diester (IV) in the presence of a base, such as triethylamine, to obtain the tri-ester (VI). Specific hydrolysis of the carboxylate ester group, as by base, affords the diester (VII; $R_1$ and $R_2$ do not equal H). Controlled removal of one of those ester groups, as by catalytic hydrogenolysis, with base, or with iodide salts by the method of L. Zervas, et al, J. Am. Chem. Soc. 77, 5354 (1955) yields the mono ester (VII; $R_1$ is not equal to H, $R_2$=H). Alternately, compound (IV) may be condensed with compound (II) to afford compound (VII) directly.

Method III

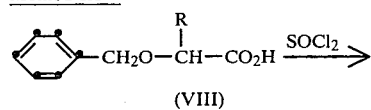

(VIII)

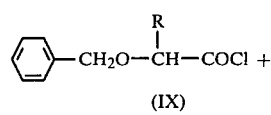

(IX)

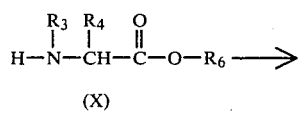

(X)

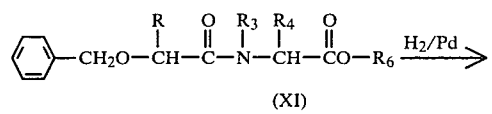

(XI)

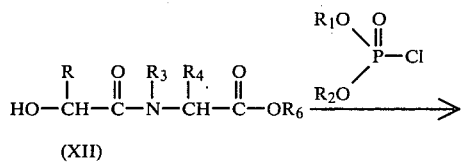

(XII)

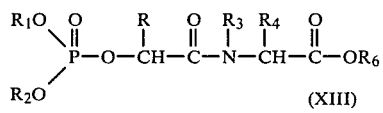

(XIII)

Then, when $R_1=R_2$=phenyl and $R_6$=t-butyl:

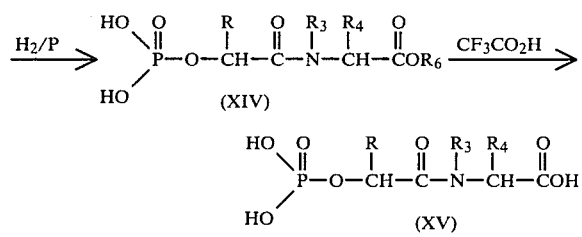

In this process, a 2-benzyloxy acetic acid derivative (VIII), which can be prepared from the corresponding 2-hydroxyacetic acid derivative, is reacted with thionyl chloride to produce the acid chloride (IX), which is then reacted with an ester (X) in a solvent such as methylene chloride containing a base, like triethylamine, to obtain the ester (XI). The ester is then converted to the hydroxy compound (XII) by use of hydrogen and a palladium catalyst in a conventional manner.

Alternately, compounds of structure XII may be obtained by coupling the unprotected hydroxy acetic acid derivative corresponding to VIII directly with the amino acid ester X by means of dicyclohexyl carbodiimide or a similar reagent. This hydroxy compound is reacted with a diaryl or diaryalkyl or dialkyl chlorophosphate in a solvent such as ether containing a base, like pyridine to yield the ester (XIII). When $R_1=R_2$=phenyl and $R_6$=t-butyl (XIII) is converted to the ester (XIV) by the use of hydrogen and a platinum catalyst in a conventional manner, and (XIV) is then converted to the acid (XV) by treatment with a strong acid, such as trifluoroacetic acid.

Alternately compound XII may be reacted with phosphorous oxychloride under basic conditions and hydrolyzed to obtain compound XV.

Method IV

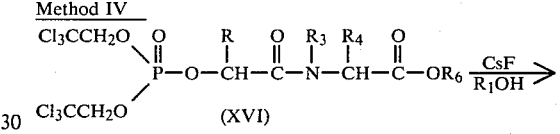

(XVI)

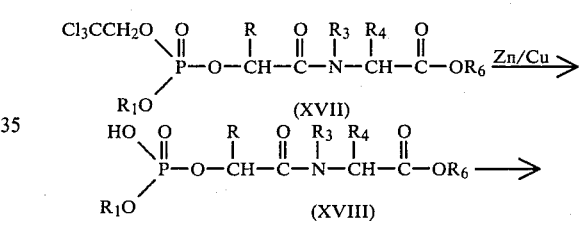

(XVII)

(XVIII)

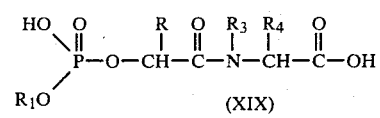

(XIX)

In this process, the bis-trichloroethyl ester (XVI) prepared as described above for (XII) is converted to the monotrichloroethyl ester (XVII) by a procedure described by K. K. Ogelvie, et al., J. Am. Chem. Soc. 99, 1277 (1977). The trichloroethyl function is then removed using a process described by A. Franke, et al., Chem. Ber., 101, 944 (1968). The ester (XVIII) is then hydrolyzed to (XIX) using standard procedures.

Alternatively, the hydroxy compound XII may be treated with an alkyl, aryl or aralkyl phosphodichloridate and hydrolyzed in aqueous base to obtain the mono-ester XIX.

Method V

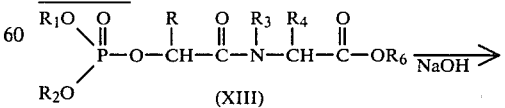

(XIII)

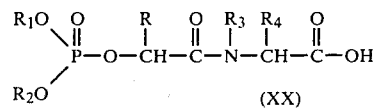

(XX)

In this process, (XIII), prepared as described above, is hydrolyzed to the carboxylic acid derivative (XX) by a controlled basic hydrolysis.

Method VI

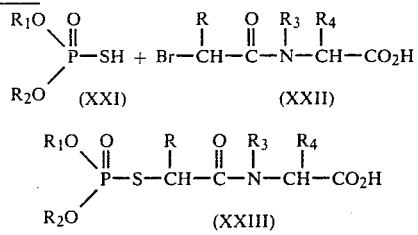

In this process, a thiophosphoric acid derivative (XXI) is reacted with a bromo (or iodo) compound (XXII) in a process like that described by S. Akerfeldt, Acta Chem. Scand., 16, 1897 (1962).

Products of general Formula (I) have up to two asymmetric carbons, namely, the carbon atoms to which R and $R_4$ are attached, when R and $R_4$ are other than hydrogen. The compounds accordingly exist in diastereoisomeric forms or in racemic mixtures thereof. All of these are within the scope of the invention. The above described syntheses can utilize the racemate or one of the enantiomers as starting material. When the racemic starting material is used in the synthetic procedure, the stereoisomers obtained in the product can be separated by conventional chromatographic or fractional crystallization methods.

In general, the amino acid part-structures, i.e.,

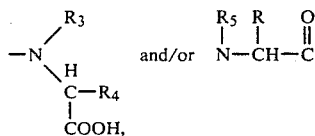

of Formula (I) are preferred in the L-configuration. These preferred configurations also apply to homolog amino acids and when X is 0 or S replacing $NR_5$. Specifically when X is 0 or S the configuration is that of L-lactic or L-thiolactic acid respectively.

The compounds of this invention form basic salts with various inorganic and organic bases which are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine salts, N-methyl-D-glucamine, salts with amino acids like arginine, lysine and the like. The non-toxic physiologically acceptable salts are preferred, although other salts are also useful, e.g., in isolating or purifying the product, as illustrated in the examples in the case of the dicyclohexylamine salt.

The salts may be formed by conventional means, as by reacting the free acid form of the product with one or more equivalents of the appropriate base in a solvent or medium in which the salt is insoluble, or in water and removing the water by freeze drying, or by exchanging the cations of an existing salt for another cation on a suitable ion exchange resin.

The compounds of this invention inhibit angiotensin converting enzyme and thus block conversion of the decapeptide angiotensin 1 to angiotensin 2 and inhibit the degradation of bradykinin. Thus, the present compounds are useful as antihypertensives in treating hypertensive mammals, including humans.

The compounds of this invention can be utilized to achieve the reduction of blood pressure by formulating in compositions such as tablets, capsules or elixirs for oral administration or in sterile solutions or suspensions for parenteral administration. About 10 to 500 mg. of a compound or mixture of compounds of Formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as calcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc. or a synthetic fatty vehicle like ethyl oleate or the like. Buffers, preservatives, antioxidants and the like can be incorporated as required.

The following examples are illustrative of the invention and constitute especially preferred embodiments. All temperatures are in degrees Celsius.

EXAMPLE 1

N-[N'-Phosphoryl-L-Alanyl]-L-Alanine, Magnesium Salt

Dissolve 228 mg. of L-alanyl-L-alanine in 5 ml. ice water. While stirring the solution, add 400 mg. magnesium oxide. Add 0.175 ml phosphorus oxychloride in carbon tetrachloride over a 30 min. period. Continue stirring the mixture for 1 hour at 0°. Filter the mixture, washing the precipitate with 20 ml water. Adjust the pH of the combined filtrate and washings to 7.0 with sodium hydroxide. Add twice the volume of absolute ethanol, centrifuge the mixture, and discard the solids. Lyophilize the supernatant liquid to obtain the product. Yield 31 mg. Phosphate determination by the method of W. P. Jencks and M. Gilchrist, J. Amer. Chem. Soc. 86, 1410 (1964) showed the material to contain 35% of N-[N'-Phosphoryl-L-alanyl]-L-alanine.

EXAMPLE 2

N-(Dibenzylphosphoryl-L-Alanyl)-L-Proline, Ammonium Salt

Prepare a fresh solution of dibenzylphosphochloridate from 1.46 g. (5.6 mmoles) of dibenzyl phosphite in 20 ml of methylene chloride by the method of G. W. Kenner et al., J. Chem. Soc. 1952, 3675. Add 1.56 g (5.0 mmoles) of benzyl L-alanyl-L-prolinate hydrochloride dissolved in 20 ml of methylene chloride, then 1.4 ml (10 mmoles) of triethylamine, and stir at room temperature for one hour. Remove volatiles in vacuo in a rotary evaporator, triturate with 125 ml of ether, filter and discard the solids. Wash the ether solution 4× with 30 ml of aqueous 1% sodium bicarbonate, dry over anhydrous $Na_2SO_4$, and concentrate to dryness. Yield 2.7 g of tri-ester.

Dissolve this material in a mixture of 90 ml of acetonitrile and 72 ml of water. Add 15 ml of 1 M NaOH and stir for 5 hours at room temperature. Neutralize to pH 8.8 with 9 ml of 1 M HCl, concentrate to a volume of about 50 ml in a rotary evaporator, and freeze dry. Yield 2.9 g of crude product. Purify 150 mg of this crude product by gel filtration chromatography on a column of Sephadex LH-20 eluting with water containing 1 g/l of $NH_4HCO_3$ and combining the product fractions, as determined by U.V. detection. Freeze-dry, dissolve the residue in 1 ml of the above solvent, and purify further by chromatography on a column of XAD-2 resin, developing with a linear gradient of water-acetonitrile of from 0% to 90% acetonitrile. Combine the product fractions and remove the solvent in vacuo. Yield 80 mg of N-(dibenzylphosphoryl-L-alanyl)-L-proline, ammonium salt.

pmr Spectrum ($NH_4^+$) salt, $D_2O$, MeOH internal standard): 1.20 ppm (d,J=6,3H), 1.45–2.05 (broad m, 4H), 2.52–3.43 (broad M,2H), 3.43–4.18 (broad m, 2H), an absorbance partly masked by water peak at 4.67 ppm, 7.13 (S, 10H).

EXAMPLE 3

N-(Benzylphosphoryl-L-Alanyl)-L-proline, di-Ammonium Salt

Suspend 60 mg of 10% Pd on carbon catalyst in 10 ml of 50% (v/v) aqueous dioxane, add 0.28 ml of triethylamine, and pre-reduce the catalyst with hydrogen for 3 hours. Dissolve 472 mg (1.1 mmole) of the purified dibenzyl ester prepared as described above in 10 ml of 50% aqueous dioxane, adjust the pH to 9.0 with a little triethylamine, add to the above catalyst suspension, and hydrogenate at atmospheric pressure and room temperature until just one millimole of hydrogen has been absorbed, about 8–10 minutes. Stop the hydrogenation, filter, concentrate and flush with water on a rotary evaporator to remove dioxane, and freeze-dry.

Dissolve the crude product in 0.1% aqueous ammonium bicarbonate solution and pass over a column of 10 g of Dowex 50 ($NH_4^+$), eluting with the same solvent. Freeze-dry the pooled product fractions (U.V. detection) and chromatograph on a column of XAD-2 resin, eluting with a linear gradient of 0.1% aqueous $NH_4HCO_3$-acetonitrile 0–90%. Combine the product fractions (U.V.) concentrate and flush with water on a rotary evaporator, and freeze-dry. Yield of N-(benzylphosphoryl-L-alanyl)-L-proline diammonium salt 312 mg.

pmr ($D_2O$, NaOD, dioxane internal standard): 1.32 ppm (d,J=6,3H), 1.60–2.23 (m,4H), 3.23–4.33 (m, 4H), an absorbance partly masked by water peak at 4.75 ppm, 7.47 (S, 5H).

EXAMPLE 4

N-(Diphenylphosphoryl-L-Alanyl)-L-Proline, Ammonium Salt

Cool to 0° a solution of 200 mg (1.07 mmole) of L-alanyl-L-proline in 5 ml of methylene chloride, add 0.3 ml (2.14 moles) of triethylamine, then a solution of 287 mg (1.07 mmoles) of diphenylphosphochloridate in 5 ml of cold methylene chloride. Stir for 2 hours, then add dropwise with good stirring to a solution of 237 mg (3 mmoles) of ammonium bicarbonate in 10 ml of water, making certain that the pH remains above 7.8. Distill off the methylene chloride and pass the aqueous solution through a column of Dowex 50 ($NH_4^+$). Concentrate the fractions containing the product (U.V. detection) in vacuo to a small volume, then freeze-dry.

Mass spectrometry on the trimethylsilyl derivative shows a molecular ion at M/e=490 (M+TMS) and an appropriate fragmentation pattern.

EXAMPLE 5

N-(Phenylphosphoryl-L-Alanyl)-L-Proline, disodium salt

Take up 1.0 g (3.2 mmoles) of L-alanyl-L-proline benzyl ester .HCl in 15 ml of methylene chloride, cool to 0° and add 0.7 g (7 mmoles) of triethylamine. Dissolve 0.86 g (3.2 mmoles) of diphenylphosphochloridate in 10 ml of methylene chloride, and to the above solution, and stir 2 hours at room temperature. Remove volatiles in vacuo in a rotary evaporator, triturate with 50 ml of ether, filter off and discard the solids, and concentrate the filtrate to dryness. Yield of crude product 1.57 g. Purify by chromatography on silica gel, eluting with acetone; $r_f$=0.5. Recovery 75%.

Dissolve 519 mg (1.05 mmoles) of this purified tri-ester in a mixture of 17 ml of acetonitrile and 17 ml of water. Add 3.1 ml of 1 M NaOH, stir overnight at room temperature, neutralize to pH 9 with Dowex 50 (H+) ion exchange resin, filter, concentrate in vacuo in a rotary evaporator to remove acetonitrile, wash 3× with 15 ml of ether and freeze-dry. Yield 467 mg.

pmr spectrum (disodium salt, $D_2O$, dioxane internal standard): 1.23 ppm (d,J=6,3H), 1.62–2.25 (broad m, 4H), 3.42 (t, 2H), 3.65–4.28 (broad m, 2H), 6.85–7.55 (M, 5H).

EXAMPLE 6

N-(O-phosphoryl-dl-lactoyl)-L-proline

Suspend 9.8 g. of 50% sodium hydride (dispersed in mineral oil) in 250 ml toluene contained in a flask equipped with a magnetic stir bar, thermometer, condenser, additional funnel and provision for maintaining an inert atmosphere. Dissolve 20.8 g. of methyl d,l-lactate in 50 ml toluene and add the solution dropwise over 30 min. to the sodium hydride suspension. Then add a solution of 37 g benzyl bromide in 40 ml toluene over 20 min. Raise the temperature to 87°–90° and maintain for 18 hours, then cool and concentrate the reaction mixture. Add the product to a solution of 40 ml 50% NaOH, 300 ml water and 200 ml dioxane and heat to 80° for 2 hours. Cool the reaction, adjust the pH to 8–9 with hydrochloric acid and reduce the volume in vacuo to 250 ml, then wash the solution with ether. Acidify the aqueous layer with hydrochloric acid and extract with ether. Dry the extract, concentrate in vacuo and distill the d,l-2-benzyloxy propionic acid. bp 122–124 at 0.05 mm. Yield: 25.6 g.

Treat 6.3 g of this acid with 25 ml of $SOCl_2$ at room temperature for 18 hours. Concentrate the reaction to an oil in vacuo and flush twice with benzene to obtain the crude acid chloride.

Dissolve this crude acid chloride in 50 ml $CH_2Cl_2$ and then add it dropwise to a solution of 7.3 g t-butyl-L-prolinate hydrochloride and 11 ml triethylamine in 150 ml $CH_2Cl_2$ which is cooled in an ice bath. After 4.5 hours, filter the reaction and concentrate the filtrate in vacuo. Add ether to the residue, filter and concentrate the filtrate in vacuo. Yield: 13.1 g.

Dissolve 9.6 g of this ester in 100 ml of 50% aqueous ethanol and add 4 g of 10% Pd on carbon. Hydrogenate the mixture at 40 psi constant pressure until the theoretical amount of hydrogen has been absorbed. Filter the reaction, concentrate the filtrate in vacuo and dissolve the residue in $CH_2Cl_2$. Dry this solution with $Na_2SO_4$, filter and concentrate the filtrate in vacuo to obtain the product. Yield: 7.1 g.

Dissolve 0.98 g of this hydroxy ester in 10 ml ether and add it dropwise to a solution of 1.08 g diphenyl phosphochloridate in 15 ml pyridine which is chilled in an ice bath. Allow the reaction to slowly reach room temperature and then continue stirring the reaction for an additional 19 hours. Concentrate the reaction in vacuo and triturate the residue with ether, then filter and concentrate the filtrate in vacuo. Chromotograph the crude product on silica gel with 1:1 ethyl acetate: hexane. Yield: 1.48 g.

Dissolve 0.95 g of this diphenylphosphate ester in 25 ml glacial acetic acid and add 0.3 g of platinum oxide. Hydrogenate the mixture at 24° starting at an initial pressure of 40 psi. Filter the reaction, concentrate the filtrate in vacuo, dissolve the residue in $H_2O$, and freeze-dry. Isolate 471 mg of white solid.

Treat 170 mg of the above phosphate ester with 2 ml of trifluoroacetic acid at room temperature for 2 hours. Concentrate the reaction in vacuo, dissolve the residue in water and freeze-dry to obtain the N-(O-phosphoryl-d,l-lactoyl)-L-proline.

pmr in $D_2O$: 1.37 ppm (doublet, J=6, 3H); 1.7–2.3 (broad m, 4H); 3.25–3.85 (broad m, 2H); 4.2–4.5 (broad m, 1H), 4.7–5.2 (m partially obscured by $H_2O$, $J_{H-H}=7$, $J_{P-H}=7$,

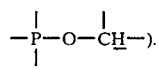

EXAMPLE 7

N-(O-Diphenylphosphoryl-d,l-lactoyl)-L-Proline

Dissolve 110 mg of t-butyl N-(O-diphenylphosphoryl-d,l-lactoryl)-L-prolinate, as prepared in Example 6, in 1.5 ml trifluoroacetic acid. Stir the reaction for 1.5 hr. at room temperature, then concentrate and flush with $CCl_4$. Obtain the product as a clear oil.

pmr in $DCCl_3$: 1.53 ppm (doublet, J=6, 3H); 1.8–2.4 ppm (broad, 4H); 3.35–3.8 ppm (broad, m, 2H); 4.4–4.6 (broad, m, 1H) 5.0–5.6 (m, $J_{HH}=6$); 7.25 (S, 10H).

EXAMPLE 8

N-(O-Benzylphosphoryl-d,l-lactoyl)-L-Proline

Dissolve 1.85 g. of methyl N-(bis-(2,2,2-trichloroethyl)phosphoryl-d,l-lactoyl)-L-prolinate, prepared by the method described in Example 6 above in 21 ml benzyl alcohol containing 4.7 g. cesium fluoride. Stir this mixture at room temperature for 24 hr. Then dilute the reaction with ether and wash with $H_2O$ and brine. Dry the organic layer over $CaCl_2$ filter and concentrate. Remove the residual benzyl alcohol under high vacuum and obtain the product as a clear oil.

Dissole 0.5 g. of this mixed tri-ester in 30 ml dry dimethylformamide and heat the solution to 55°. Add 4 g. of zinc-copper couple and then stir the mixture at 55° for 1 hour. Remove the solvent under high vacuum. Dissolve the residue in aqueous acetonitrile and pass the solution over a column of Dowex 50×2 ion exchange resin on the acid cycle. Collect and concentrate those fractions which contain the P-monobenzyl-C-methyl diester.

Add 100 mg. of this material to 15 ml of 0.5 M NaOH, stir the mixture at room temperature for 3 hrs., bring the reaction to pH 7–8 with Dowex 50 (H+) resin, concentrate and pass the residue over a column of Dowex 50×2 on the acid cycle eluting with water. Collect and concentrate those fractions which contain the monobenzyl ester.

EXAMPLE 9

N-(Benzylphosphoryl-L-Alanyl)-L-Thiazolidine-4-carboxylic acid, di-ammonium salt Starting with 1.46 g of dibenzyl phosphite and 1.66 g of benzyl N-(L-alanyl)-L-thiazolidine-4-carboxylate hydrochloride made by standard peptide techniques, prepare benzyl N-(dibenzylphosphoryl-L-alanyl)-L-thiazolidine-4-carboxylate by the procedure described in Example 2 above.

Reflux a mixture of 1.11 g (2.0 mmoles) of this tri-ester and 0.33 g of sodium iodide in 7 ml of acetone for 30 minutes. Concentrate the mixture to dryness in vacuo in a rotary evaporator, triturate the residue with 2×15 ml of ether, and discard the extracts. Take up the solids in 40 ml of 0.1 M sodium hydroxide, stir 4 hours at room temperature, neutralize to pH 8.5 with acetic acid, wash with 2×10 ml of ether, and freeze-dry. Dissolve the residue in a few ml of 0.1% ammonium bicarbonate solution and pass through a column of Dowex 50 ($NH_4^+$). Combine product fractions (U.V. detection), concentrate in vacuo, and freeze-dry to obtain the di-ammonium salt of N-(benzylphosphoryl-L-alanyl)-L-thiazolidine-4-carboxylate.

EXAMPLE 10

In general in the above examples, L-proline may be replaced by L-thiazolidine-4-carboxylic acid; the products then obtained are "thioproline" analogs, in which $R_3$ and $R_4$ of Formula (I) comprise a $-CH_2-S-CH_2$ bridge.

EXAMPLE 11

N-[O-(O'-Benzylphosphoryl)lactoyl]thiazolidine-4-carboxylic acid

Dissolve 3.67 g methyl L-thiazolidine-4-carboxylate hydrochloride in a mixture of 75 ml $CH_2Cl_2$ and 2.8 ml triethylamine. Cool this solution in an ice bath and add 2.70 g d,l-lactic acid and 4.5 g dicyclohexylcarbodiimide. Stir this mixture for 20 hours at 0°. Concentrate the reaction mixture in vacuo, add ice cold ether to the residue and filter. Wash the filtrate with sodium bicarbonate solution, dry the organic phase over Na₂SO₄, filter, and concentrate the filtrate in vacuo to obtain the product as an oil.

Dissolve 1.10 g of the above hydroxy ester in 25 ml ether and add the solution dropwise to an ice cold solution of benzylphosphodichloridate in 10 ml pyridine and 15 ml ether. Stir the reaction for 5 hours at 0°, filter, and concentrate the filtrate in vacuo. Dissolve the residue in 25 ml dioxane and add the solution to 50 ml 2 M NaOH. Stir the mixture at room temperature for 3 hours, then make to pH 7-8 by the addition of Dowex 50×2 resin on the acid cycle. Filter the mixture, concentrate the filtrate in vacuo to 5-6 ml and chromatograph on a Dowex 50×2 ion exchange resin on the acid cycle. Collect those fractions containing the phosphate diester (U.V. detection) and freeze dry to obtain the product as a powder.

EXAMPLE 12

N-(O-Phosphoryllactoyl)thiazolidine-4-carboxylic acid

Dissolve 1.10 g methyl N-(d,l-lactoyl)thiazolidine-4-carboxylate, prepared as described above in Example 11, in 25 ml ether and add the solution dropwise to a well cooled solution of 3.0 g freshly distilled phosphorous oxychloride and 10 ml pyridine in 15 ml ether. After the addition is completed, remove the cooling bath and stir the reaction an additional 20 hours. Concentrate the reaction in vacuo at 40° C. Flush the reaction product several times with benzene and finally remove residual volatiles at 1 mm pressure. Dissolve the residue in 20 ml dioxane and add the solution to 25 ml 2 M NaOH. Stir the solution for 4 hours at room temperature, adjust the pH to 7-8 by the addition of Doxex 50×2 resin on the acid cycle, filter, and concentrate the filtrate to a volume of 5-6 ml. Chromatograph this solution on Dowex 50×2 ion exchange resin on the acid cycle. Freeze dry those fractions containing the product to obtain the phosphate as a solid.

EXAMPLE 13

N-(Methylphosphoryl-L-Alanyl)-L-Proline,Di-Sodium Salt

To a solution of 35.7 g (.24 mole) of methyl phosphodichloridate in 200 ml of methylene chloride cooled to −15° C. add dropwise over 1 hour a solution of 12.5 g (.04 moles) of benzyl alanylprolinate hydrochloride and 8.5 g (0.084 moles) of triethylamine. Bring to room temperature and hold for 1¼ hours. Add this solution dropwise with good stirring to 600 ml of water, holding the pH at 8-9 by adding 1 M NaOH as needed. Separate the layers wash the water solution with fresh methylene chloride, concentrate in vacuo, and freeze-dry. Pass a solution of this crude product over a column of Dowex 50 (Na+), eluting with water. Combine and concentrate the product fractions to a small volume and purify further by chromatography on XAD-2 resin, again eluting with water. Combine the product fractions (U.V. detection), concentrate to a smaller volume, and hydrolyze the benzyl ester by adjusting and holding the pH at 10.5-11.0 for 2 hours by adding 1 M NaOH as necessary. Neutralize to pH 8.8 with a small amount of Dowex 50(H+) resin, extract the solution 3× with ether and discard the extract. Concentrate the solution to a smaller volume and freeze-dry to obtain the N-(methylphosphoryl-L-alanyl)-L-proline disodium salt.

EXAMPLE 14

N-(Methylphosphoryl-L-Alanyl)-L-Alanine, Di-Sodium Salt

When benzyl L-alanyl-L-alaninate hydrochloride is substituted for benzyl 2-alanyl-L-prolinate in Example 13, the identical process affords N-(methylphosphoryl-L-alanyl)-L-alanine disodium salt.

EXAMPLE 15

N-(Diethylphosphoryl-L-Alanyl)-L-Proline, Ammonium Salt

To a solution of 1.0 g (5.8 mmole) of diethyl phosphochloridate in 20 ml of methylene chloride add a solution of 1.62 g (5.2 mmole) of benzyl L-alanyl-L-prolinate.HCl in 20 ml of methylene chloride. Then add 1.46 ml (11.6 mmole) of triethylamine and stir 1 hour at room temperature. Strip off the volatiles in vacuo, triturate with 125 ml of ether, discard the solids, and wash the ether solution with dilute sodium bicarbonate solution. Dry over anhydrous Na₂SO₄ and distill off the ether on a rotary evaporator to obtain the tri-ester.

Dissolve this material in 120 ml of 50% aqueous acetonitrile, add 10 ml of 1 M NaOH, stir 5 hours at room temperature, neutralize to pH 8.8 with 1 M HCl, wash 3× with 50 ml of ether, concentrate in vacuo to a small volume, and freeze-dry. Purify this crude product by chromatography on a column of Sephadex LH-20, eluting with water containing 0.1% NH₄HCO₃, combine the product fractions, and freeze-dry to obtain the N-(diethylphosphoryl-L-alanyl)-L-proline as its ammonium salt.

EXAMPLE 16

| Dry filled capsules containing 50 mg of active ingredient per capsule | |
|---|---|
| | Per Capsule |
| N-(phenylphosphoryl-L-alanyl)-L-proline disodium salt | 50 mg. |
| Lactose | 149 mg. |
| Magnesium Stearate | 1 mg. |
| Capsule (Size No. 1) | 200 mg. |

The N-(phenylphosphoryl-L-alanyl)-L-proline disodium salt is reduced to a No. 60 powder and then lactose and magnesium stearate are passed through a No. 60 bolting cloth onto the powder and the combined ingredients admixed for 10 minutes and then filled into a No. 1 dry gelatin capsule.

What is claimed is:

1. A compound of the formula:

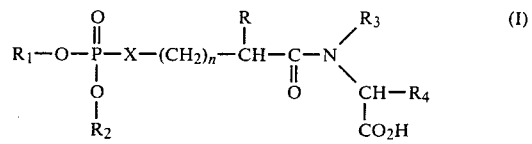

wherein n is 0 or 1

R is lower alkyl, phenyl lower alkyl, hydroxyphenyl lower alkyl, hydroxy lower alkyl, aminoloweralkyl, guanidino lower alkyl, imidazoyl lower alkyl, indolyl lower alkyl, mercapto lower alkyl, lower alkyl mercapto lower alkyl;

R₃ and R₄ may be connected together to form an alkylene bridge of from 2 to 4 carbon atoms or an alkylene bridge of from 2 to 3 carbon atoms and one sulfur atom;

X is NR⁵, S where R⁵=H or lower alkyl;

R₁ is hydrogen, lower alkyl, phenyl lower alkyl or phenyl or substituted phenyl wherein the substituent is halo, lower alkoxy or lower alkyl;

R₂ is hydrogen, lower alkyl, phenyl lower alkyl, or phenyl or substituted phenyl wherein the substituent is halo, lower alkoxy or lower alkyl and pharmaceutically acceptable salts thereof.

2. A compound of claim 1 wherein R₃ and R₄ are joined to form

wherein

Y is CH₂ or S;

X is NR₅ and

R is lower alkyl or phenyl (C₁₋₄)lower alkyl.

3. A compound of claim 2 wherein R is methyl, X is NH and n=0.

4. A compound of claim 3 having the formula

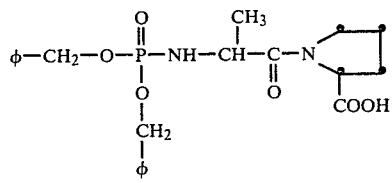

and the pharmaceutically acceptable salts thereof.

5. A compound of claim 3 having the formula

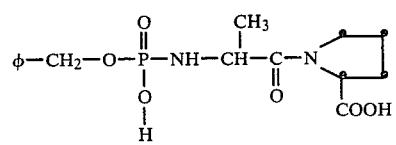

and the pharmaceutically acceptable salts thereof.

6. A compound of claim 3 having the formula:

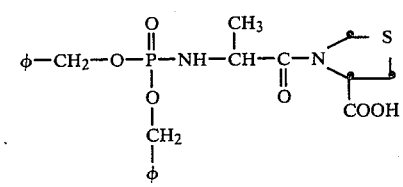

and the pharmaceutically acceptable salts thereof.

7. A compound of claim 3 having the formula:

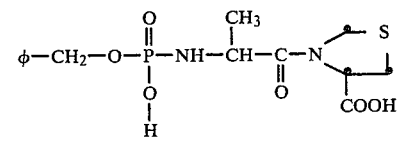

and the pharmaceutically acceptable salts thereof.

8. A compound of claim 3 with X=NH of the L-amino acid configurations.

9. A pharmaceutical composition for treating hypertension comprising a pharmaceutically acceptable carrier and an antihypertensively effective amount of a compound of claim 1.

* * * * *